United States Patent
Vågberg et al.

(10) Patent No.: US 12,264,165 B2
(45) Date of Patent: *Apr. 1, 2025

(54) PROCESS FOR THE STEREOSELECTIVE PREPARATION OF CHIRAL 2-[(HETERO)ARYLALKYLSULFANYL]PYRIMIDINES AND PRODUCTS OBTAINABLE THEREFROM

(71) Applicant: KANCERA AB, Solna (SE)

(72) Inventors: Jan Vågberg, Solna (SE); Styrbjörn Byström, Solna (SE)

(73) Assignee: Kancera AB, Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/199,899

(22) Filed: May 19, 2023

(65) Prior Publication Data
US 2023/0322807 A1    Oct. 12, 2023

Related U.S. Application Data (63) Continuation of application No. 17/966,294, filed on Oct. 14, 2022, now Pat. No. 11,691,988, which is a continuation of application No. 17/055,172, filed as application No. PCT/EP2019/062530 on May 15, 2019, now Pat. No. 11,542,281.

(30) Foreign Application Priority Data

May 15, 2018   (GB) ..................... 1807898

(51) Int. Cl.
C07D 513/04   (2006.01)
C07D 239/56   (2006.01)

(52) U.S. Cl.
CPC ......... *C07D 513/04* (2013.01); *C07D 239/56* (2013.01)

(58) Field of Classification Search
CPC .................................. C07D 513/04
USPC ........................................ 544/255
See application file for complete search history.

(56) References Cited

U.S. PATENT DOCUMENTS 11,691,988 B2 * 7/2023 Vågberg .............. C07D 239/56
544/255

FOREIGN PATENT DOCUMENTS

| | | |
|---|---|---|
| AU | 2019270348 A | 5/2019 |
| CA | 3099865 A1 | 5/2019 |
| CN | 112218853 A | 5/2019 |
| EP | 3793981 A1 | 5/2019 |
| GB | 1807898.0 | 5/2018 |
| IL | 278644 B1 | 5/2019 |
| JP | 7225379 B2 | 5/2019 |
| KR | 20210014646 A | 5/2019 |
| MX | 2020012108 A | 5/2019 |
| SG | 11202011317 | 5/2019 |
| WO | WO 2000/09511 | 2/2000 |
| WO | WO 2004/011443 A1 | 2/2004 |
| WO | WO 2006/107258 A1 | 12/2006 |
| WO | PCT/EP2019/062530 | 5/2019 |
| ZA | 202007101 B | 11/2020 |

OTHER PUBLICATIONS

U.S. Appl. No. 17/055,172, filed Nov. 13, 2020, Jan Vågberg.
U.S. Appl. No. 17/966,294, filed Oct. 14, 2022, Jan Vågberg.
Karlström, Sofia et al., "Substituted 7-Amino-5-thio-thiazolo[4,5-d]pyrimidines as Potent and Selective Antagonists of the Fractalkine Receptor (CX3CR1)," J. Med. Chem. (2013), vol. 56, No. 8, pp. 3177-3190 (14 pages).
International Search Report and Written Opinion mailed on Jul. 17, 2019 for Patent Application No. PCT/EP2019/062530, which was filed on May 15, 2019 and published as WO 2019/219771 on Nov. 21, 2019 (Inventor—Vågberg et al.; Applicant—Kancera AB) (10 pages).

* cited by examiner

*Primary Examiner* — Kahsay Habte
(74) *Attorney, Agent, or Firm* — Ballard Spahr LLP (57) ABSTRACT

Described herein is a process for the preparation of a compound of Formula I,

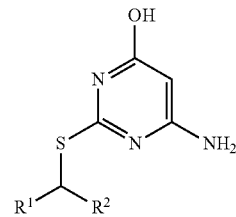

Formula I wherein $R^1$ and $R^2$ each have the meanings provided in the description. Also described is a process for the preparation of pharmaceutically-active compounds including the process for the preparation of compounds of Formula I.

4 Claims, 2 Drawing Sheets

PROCESS FOR THE STEREOSELECTIVE PREPARATION OF CHIRAL 2-[(HETERO) ARYLALKYLSULFANYL]PYRIMIDINES AND PRODUCTS OBTAINABLE THEREFROM

CROSS-REFERENCE TO RELATED APPLICATIONS

This application is a continuation of U.S. application Ser. No. 17/966,294, filed Oct. 14, 2022, which is a continuation of U.S. application Ser. No. 17/055,172, filed Nov. 13, 2020, which is a U.S. National Phase Application of International Application No. PCT/EP2019/062530, filed May 15, 2019, which claims priority to Great Britain Application No. 1807898.0, filed May 15, 2018, each of which are hereby incorporated by reference in their entirety

FIELD OF THE INVENTION

The present invention relates to new synthetic methods for obtaining compounds with high chiral purity. In particular, it relates to processes for the production of chiral pyrimidines and their use as intermediates in the preparation of pharmaceutically-active compounds.

BACKGROUND OF THE INVENTION

The listing or discussion of an apparently prior-published document in this specification should not necessarily be taken as an acknowledgement that the document is part of the state of the art or is common general knowledge.

7-Amino-5-thio-thiazolo[4,5-d]pyrimidines are known to be antagonists of the fractalkine receptor (Karlström et al. *J. Med. Chem.*, 2013, 56, 3177-3190). Among these compounds, those containing chiral α-alkyl branched benzyl thioether groups are of considerable interest. In particular, the compound (2R)-2-[(2-amino-5-{[(1S)-1-phenylethyl]thio}[1,3]thiazolo[4,5-d]pyrimidin-7-yl)amino]-4-methylpentan-1-ol is known to be a potent antagonist.

The stereocentre at the top of the molecule can be set by using the desired enantiomer of leucinol (which derives from the amino acid leucine, and is available with very high enantiomer purity). However, providing a scalable route that provides sufficient chiral purity at the second stereocentre (marked with *) has proved a significant challenge.

In the published laboratory-scale route (Karlström et al.), the stereochemistry of this chiral centre is set in the final step through the reaction of the thiothiazolopyrimidine intermediate with (R)-1-chloroethylbenzene, which yields a 9:1 ratio of diastereomers in favour of the desired R,S-diastereomer. Purification by chiral HPLC then gave the desired compound with a chiral purity of 99.7%. However, it is not feasible to perform chiral HPLC on the scale required for the production of active pharmaceutical ingredients.

The basic route to 6-Amino-2-{[(1S)-1-phenylethyl]sulfanyl}pyrimidin-4-ol is published in WO 2006/107258.

However, scale up of known methods are likely to yield lower chiral purity materials. While purer materials might be prepared, up to a limit, by e.g. successive recrystallisation steps, such purification steps would greatly reduce the yield of the process and are also highly undesirable in a chemical production process.

DISCLOSURE OF THE INVENTION

We have now surprisingly found that (hetero)arylalkylsulfanylpyrimidines, such as 6-amino-2-{[(1S)-1-phenylethyl]sulfanyl}pyrimidin-4-ol, can be obtained in good yields and with excellent chiral purity, without the need for additional recrystallisation steps, by preparing a corresponding (hetero)arylalkylsulfonate ester under carefully selected reaction conditions, and the subsequent reaction of this species with the required pyrimidine thiolate anion.

This process provides a simple and scalable route to synthetic intermediates that allow for the production of pharmaceutically-interesting compounds, such as (2R)-2-[(2-amino-5-{[(1S)-1-phenylethyl]thio}[1,3]thiazolo[4,5-d]pyrimidin-7-yl)amino]-4-methylpentan-1-ol with very high chiral purity.

New Processes

In a first aspect of the invention there is provided a process for the preparation of compound of formula I, or a salt thereof, wherein
$R^1$ represents aryl or pyridyl optionally substituted with one or more groups selected from halo, —CN, —C(O)NR³R⁴, —S(O)₂R⁵; $C_{1-6}$ alkyl, $C_{2-6}$ alkenyl, $C_{2-6}$ alkynyl, wherein the latter three groups are optionally substituted by one or more F;
$R^2$ represents $C_{1-6}$ alkyl optionally substituted by one or more F;
$R^3$ and $R^4$ each independently represent H or $C_{1-6}$ alkyl optionally substituted by one or more F;
$R^5$ represents $C_{1-6}$ alkyl optionally substituted by one or more F;
which process comprises the steps of:
(i) forming a compound of formula II wherein $R^1$ and $R^2$ are as defined for a compound of formula I and $R^6$ represents $C_{1-6}$ alkyl optionally substituted by one or more F, or phenyl optionally substituted by one or more groups selected from halo, methyl and —$NO_2$;

by reacting a compound of formula III (III)

wherein $R^1$ and $R^2$ are as defined for a compound of formula I or II;

with a suitable sulfonating agent in the presence of a suitable base $B^1$ and a suitable solvent ($S^1$) in which the salt formed between $B^1$ and the leaving group of the sulfonating agent is insoluble, and subsequently (ii) reacting the compound of formula II, with a compound of formula IV, (IV)

wherein $M^+$ represents $Li^+$, $Na^+$, $K^+$ or $Cs^+$;

wherein the compound of formula III is provided as a single enantiomer, which process may be referred to herein as "the process of the invention".

Unless indicated otherwise, all technical and scientific terms used herein will have their common meaning as understood by one of ordinary skill in the art to which this invention pertains.

Salts of the compounds produced by the processes described herein (i.e. compounds of formula I, Ia and others as defined herein) include acid and base addition salts. Such salts may be formed by conventional means, for example by reaction of a free base form of a compound of the invention with one or more equivalents of an appropriate acid, optionally in a solvent, or in a medium in which the salt is insoluble, followed by removal of said solvent, or said medium, using standard techniques (e.g. in vacuo, by freeze-drying or by filtration). Salts may also be prepared using techniques known to those skilled in the art, such as by exchanging a counter-ion of a compound of the invention in the form of a salt with another counter-ion, for example using a suitable ion exchange resin.

Particular acid addition salts that may be mentioned include those formed by reaction with corresponding acids, thus protonating the compound of the invention, to form carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxy-benzoate, salicylate, nicotinate, isonicotinate, cinnamate, oxalate, malonate, succinate, suberate, sebacate, fumarate, malate, maleate, hydroxymaleate, hippurate, phthalate or terephthalate salts), hydrogenhalide salts (e.g. hydrochloride, hyrdrobromide or hydroiodide salts), sulphonate salts (e.g. benzenesulphonate, methyl-, bromo- or chloro-benzenesulphonate, xylenesulphonate, methanesulphonate, ethanesulphonate, propanesulphonate, hydroxy-ethanesulphonate, 1- or 2-naphthalene-sulphonate or 1,5-naphthalene-disulphonate salts) or sulphate, pyrosulphate, bisulphate, sulphite, bisulphite, phosphate, monohydrogenphosphate, dihydrogenphosphate, metaphosphate, pyrophosphate or nitrate salts, and the like.

Particular base addition salts that may be mentioned include salts formed by reaction with corresponding bases, thus removing a proton from compounds of the invention, to form salts with alkali metals (such as Na and K salts), alkaline earth metals (such as Mg and Ca salts), organic bases (such as ethanolamine, diethanolamine, triethanolamine, tromethamine and lysine) and inorganic bases (such as ammonia and aluminium hydroxide). More particularly, base addition salts that may be mentioned include Mg, Ca and, most particularly, K and Na salts.

More particular salts that may be mentioned include hydrochloride, hydrobromide, sodium, potassium and lithium salts.

Unless otherwise specified, $C_{1-z}$ alkyl groups (where z is the upper limit of the range) defined herein may be straight-chain or, when there is a sufficient number (i.e. a minimum of two or three, as appropriate) of carbon atoms, be branched-chain, and/or cyclic (so forming a $C_{3-z}$ cycloalkyl group). When there is a sufficient number (i.e. a minimum of four) of carbon atoms, such groups may also be part cyclic (so forming a $C_{4-z}$ partial cycloalkyl group). For example, cycloalkyl groups that may be mentioned include cyclopropyl, cyclopentyl and cyclohexyl. Similarly, part cyclic alkyl groups (which may also be referred to as "part cycloalkyl" groups) that may be mentioned include cyclopropylmethyl. When there is a sufficient number of carbon atoms, such groups may also be multicyclic (e.g. bicyclic or tricyclic) and/or spirocyclic. For the avoidance of doubt, particular alkyl groups that may be mentioned include straight chain (i.e. not branched and/or cyclic) alkyl groups.

Unless otherwise specified, $C_{2-z}$ alkenyl groups (where z is the upper limit of the range) defined herein may be straight-chain or, when there is a sufficient number (i.e. a minimum of three) of carbon atoms, be branched-chain, and/or cyclic (so forming a $C_{4-z}$ cycloalkenyl group). When there is a sufficient number (i.e. a minimum of five) of carbon atoms, such groups may also be part cyclic. For example, part cyclic alkenyl groups (which may also be referred to as "part cycloalkenyl" groups) that may be mentioned include cyclopentenylmethyl and cyclohexenyl-methyl. When there is a sufficient number of carbon atoms, such groups may also be multicyclic (e.g. bicyclic or tricyclic) or spirocyclic. For the avoidance of doubt, particular alkenyl groups that may be mentioned include straight chain (i.e. not branched and/or cyclic) alkenyl groups.

Unless otherwise specified, $C_{2-z}$ alkynyl groups (where z is the upper limit of the range) defined herein may be straight-chain or, when there is a sufficient number (i.e. a minimum of four) of carbon atoms, be branched-chain. For the avoidance of doubt, particular alkynyl groups that may be mentioned include straight chain (i.e. not branched and/or cyclic) alkynyl groups.

For the avoidance of doubt, unless otherwise specified, groups referred to herein as "alkyl", "alkenyl" and/or "alkynyl" will be taken as referring to the highest degree of unsaturation in a bond present in such groups. For example, such a group having a carbon-carbon double bond and, in the same group, a carbon-carbon triple bond will be referred to as "alkynyl". Alternatively, it may be particularly specified that that such groups will comprise only the degree of unsaturation specified (i.e. in one or more bond therein, as appropriate; e.g. in in one bond therein).

The skilled person will understand that the substituents present in the compound of formula I obtained from the process of the invention will depend on the substituents present in the compounds of formula II that are reacted and will be able to select appropriate starting materials accordingly.

Compounds of formula I, II and III contain an asymmetric carbon atom (*) and therefore exist in two enantiomeric forms.

The stereochemistry of this chiral centre may be defined according to the convention of using a wedged bond or a hashed bond to indicate a group facing out of or into the plane of the paper. If such a bond is used it may be understood to indicate a specific single enantiomer of the compound of formula I.

As described herein, the process of the invention produces compounds of formula I with high chiral purity (i.e. single enantiomers). Accordingly, if the stereochemistry of the chiral centre is undefined (i.e. all groups attached to the chiral centre are connected to it by flat bonds), unless otherwise specified, it may be understood to indicate that either enantiomer may be present in pure form.

Unless otherwise specified, references to single enantiomers herein (and similarly to enantiomers being present in pure form, and the like) may be understood to indicate an enantiomeric purity of at least about 90% (i.e. an enantiomeric excess (e.e) of at least about 80%), such as at least about 95%, for example at least about 97%, (e.g at least about 99% (about 98% e.e.)). More particularly, a single enantiomer may have an enantiomeric purity of at least about 99.5%, such as at least about 99.7% (99.4% e.e.).

The previous two paragraphs apply analogously to the epimeric purity at the relevant chiral centre in compounds containing more than one chiral centre.

When used herein in relation to a specific value (such as an amount), the term "about" (or similar terms, such as "approximately") will be understood as indicating that such values may vary by up to 10% (particularly, up to 5%, such as up to 1%) of the value defined. It is contemplated that, at each instance, such terms may be replaced with the notation "±10%", or the like (or by indicating a variance of a specific amount calculated based on the relevant value). It is also contemplated that, at each instance, such terms may be deleted.

In particular embodiments, the compound of formula II is not isolated from the reaction mixture from step (i) before it is used in step (ii).

The skilled person will understand that references to compounds not being isolated from the reaction mixture (such as the compound of formula II not being isolated from the reaction mixture from step (i) before it is used in step (ii)) indicate that no attempts are made to obtain the relevant compound in pure form before it is used in the next reaction step. However, certain purification steps and/or other manipulations may be performed, if appropriate, such as aqueous work up, concentrating or diluting the reaction mixture and/or filtration of the reaction mixture to remove insoluble byproducts. In particular, the phrase may be understood to indicate that the relevant compound (e.g. the compound of formula II) is introduced to the next reaction step in the form of a solution in the reaction solvent for the previous synthetic step.

Step (ii) of the process of the invention occurs with inversion of stereochemistry at the chiral centre. The skilled person will understand this to mean that the relative stereochemistry of the chiral centre is reversed in the product (i.e. the compound of formula I) when compared to the starting material (i.e. the compound of formula II (or III)). As the priority of the substituents according to the Cahn-Ingold-Prelog convention for assigning absolute stereochemistry does not change during step (ii), the absolute stereochemistry of the compound of formula I will also be opposite to that of the compound of formula II (or III).

Without wishing to be bound by theory, it is believed that step (ii) occurs through a bimolecular nucleophilic substitution ($S_N2$) reaction. As the skilled person will understand, this reaction is stereospecific and the mechanism requires that inversion of the stereochemistry of a chiral centre occurs as the leaving group (in step (ii) —$OS(O)_2R^6$) is replaced by the nucleophile (in step (ii) the anionic species in the compound of formula IV).

In particular embodiments, step (i) of the process of the invention is performed in a solvent ($S^1$) in which the salt formed between the base present in the reaction mixture ($B^1$) and the leaving group of the sulfonating agent is insoluble.

For example, if step (i) is performed using mesyl chloride (methanesulfonyl chloride) as the sulfonating (or, specifically, mesylating) agent, and triethylamine as the base ($B^1$), the salt triethylamine hydrochloride will be formed as a side product in the reaction mixture and a solvent in which this salt is insoluble is selected as $S^1$.

As used herein, the term insoluble may be understood to mean that the specified chemical substance (e.g. salt, ion or neutral compound) substantially does not dissolve in the relevant solvent at room temperature. For example, less than about 10% of the total amount of the substance is in solution, such as less than about 5% (e.g. less than about 2%).

As used herein, the term leaving group may be understood to mean the group present on the relevant sulfonating agent before the reaction takes place that is replaced by a bond to the oxygen atom of the compound of formula II.

Without wishing to be bound by theory, it is believed that selecting as $S^1$ a solvent in which the salt formed between $B^1$ and the leaving group of the sulfonating agent is insoluble may contribute to the high enantiomeric purity observed in the compound of formula I as the amount of the free anion of the leaving group of the sulfonating agent (e.g. chloride) in solution is reduced. If an anion, such as chloride, is present in the reaction mixture it may take part in undesirable nucleophilic substitution processes leading to the erosion of stereochemical purity through multiple inversions of stereochemistry.

In particular embodiments of the process of the invention, step (ii) comprises bringing a solution of a compound of formula II in a solvent $S^1$ (i.e. the reaction solvent in which the compound of formula II is formed) into association with a solution of a compound of formula IV in a suitable solvent $S^2$. In more particular embodiments, $S^2$ is the solvent in which the compound of formula IV is formed.

As used herein, references to bringing solutions into association may be understood to indicate that the solutions are mixed together in the same reaction vessel. Such mixing may involve adding one of the solutions to the other, and the addition may be over a short period of time (for example one solution may be poured into the other), or the addition may be controlled to occur over a longer period of time (for example, one solution may be added dropwise to the other).

References to dropwise addition may be understood to mean the gradual controlled addition of a solution or liquid reagent over a prolonged period of time. The skilled person will be able to determine a suitable rate of addition for a given experimental set up and set of reaction conditions.

In particular embodiments, the process further comprises the step of:
(iii) preparing a compound of formula IV by reacting a compound of formula V (V)

with a suitable base $B^2$ in the presence of a suitable solvent $S^2$.

In such instances, the compound of formula IV may not be isolated from the reaction mixture of step (iii) before it is used in step (ii). In such embodiments, the solution of a compound of formula IV is obtained from step (iii), optionally after one or more purification steps.

In more particular embodiments, the solution of a compound of formula II in $S^1$ is added to the solution of a compound of formula IV in $S^2$. More particularly, the solution of a compound of formula II is added in a dropwise manner.

In particular embodiments of the invention, steps (i) and (iii) are performed concurrently (i.e. the reactions are run in parallel).

In particular embodiments, step (ii) is performed at about room temperature. As used herein 'room temperature' may be understood to indicate the ambient temperature of the room, which will generally be about 15° C. to about 25° C., for example about 20° C. to about 25° C. (e.g. about 25° C.).

As described hereinabove, $S^1$ may be a solvent in which the salt formed between $B^1$ and the leaving group of the sulfonating agent is insoluble.

Suitable solvents for $S^1$ include ethers such as diethyl ether, methyl tert-butyl ether, 1,2-dimethoxyethane, tetrahydrofuran, 1,4-dioxane and 2-methyltetrahydrofuran. In particular embodiments, $S^1$ is diethyl ether, methyl tert-butyl ether, 1,2-dimethoxyethane, tetrahydrofuran. In preferred embodiments, the solvent is methyl tert-butyl ether.

In particular embodiments, $B^1$ is an organic amine base. Examples of suitable bases include triethylamine, N,N-diisopropylethylamine, pyridine, piperidine, N-methylpiperidine and pyrrolidine. More particular bases include triethylamine and N,N-diisopropylethylamine (e.g. triethylamine).

In particular embodiments, step (i) is performed at a temperature between about −10° C. and about 20° C., such as between about −5° C. and about 10° C. (e.g. around 0° C.). Step (i) may be performed with cooling using an ice bath. In such instances it is understood that the reaction mixture is cooled to around 0° C.±about 5° C.

In particular embodiments, $S^2$ is a polar aprotic solvent. Examples of suitable solvents include N,N-dimethylformamide, N,N-dimethylacetamide, dimethylsulfoxide and N-methyl-2-pyrrolidone. In more particular embodiments, the solvent is N,N-dimethylformamide.

$B^2$ is a Group I metal (i.e. alkali metal) salt. In particular embodiments, $B^2$ is selected from the group consisting of lithium hydroxide, lithium carbonate, sodium hydroxide, sodium carbonate, potassium hydroxide, potassium carbonate, caesium hydroxide and caesium carbonate. In more particular embodiments, $B^2$ is selected from lithium hydroxide, sodium hydroxide, potassium hydroxide and caesium hydroxide. In yet more particular embodiments, $B^2$ is sodium hydroxide.

In particular embodiments, step (iii) is performed at a temperature of about 40° C. to about 80° C., such as about 50° C. to about 75° C., for example about 55° C. to about 70° C. (e.g. about 65° C.).

In particular embodiments, $R^1$ represents aryl (e.g. phenyl) or pyridyl optionally substituted with one or more groups selected from halo (for example bromo, chloro or fluoro (e.g. chloro or fluoro), —CN, —SO$_2$Me, or —CONH$_2$. In more particular embodiments, $R^1$ represents phenyl (i.e. unsubstituted).

In particular embodiments, $R^2$ represents $C_{1-6}$ alkyl (i.e. unsubstituted). In more particular embodiments $R^2$ represents $C_{1-3}$ alkyl optionally substituted by one or more F (e.g. unsubstituted). In yet more particular embodiments, $R^2$ represents trifluoromethyl, difluoromethyl, fluoromethyl or, particularly, methyl.

In particular embodiments, $R^3$ and $R^4$ each independently represent H or $C_{1-6}$ alkyl (i.e. unsubstituted). In more particular embodiments, $R^3$ and $R^4$ each independently represent $C_{1-3}$ alkyl optionally substituted by one or more F (e.g. unsubstituted). In yet more particular embodiments, $R^3$ and $R^4$ each independently represent H, trifluoromethyl, difluoromethyl, fluoromethyl or methyl. In further particular embodiments $R^3$ and $R^4$ both represent H.

In particular embodiments, $R^5$ represents $C_{1-6}$ alkyl (i.e. unsubstituted). In more particular embodiments $R^5$ represents $C_{1-3}$ alkyl optionally substituted by one or more F (e.g. unsubstituted). In yet more particular embodiments, $R^5$ represents trifluoromethyl, difluoromethyl, fluoromethyl or, particularly, methyl.

In particular embodiments, $R^6$ represents $C_{1-4}$ alkyl optionally substituted by one or more F or phenyl optionally substituted by one or more groups selected from F, Cl, Br, methyl and —NO$_2$. In more particular embodiments, $R^6$ represents methyl, trifluoromethyl, 2,2,2-trifluorethyl, nonafluorobutyl ($CF_3CF_2CF_2CF_2$—), p-tolyl, p-nitrophenyl or p-bromophenyl. In more particular embodiments, $R^6$ represents methyl.

As used herein, sulfonating agents may be understood to indicate reagents that form sulfonate esters ($RSO_3R'$) on reaction with a compound of formula III. Such sulfonate esters are formed through the displacement of a leaving group (e.g. chloride) attached to the sulfur atom of the sulfonating agent by the oxygen atom of the compound of formula III.

Suitable sulfonating agents include sulfonic anhydrides and, particularly, sulfonyl halides (e.g. sulfonyl chlorides). Particular sulfonating agents that may be mentioned include methanesulfonic anhydride (mesyl anyhydride), methanesulfonyl chloride (mesyl chloride), trifluoromethanesulfonyl chloride (triflyl chloride), trifluoromethylsulfonic anhydride (triflic anhydride), 2,2,2-trifluoroethanesulfonyl chloride (tresyl chloride), perfluoro-1-butanesulfonyl fluoride, perfluoro-1-butanesulfonyl chloride, p-toluenesulfonyl chloride (tosyl chloride), p-toluenesulfonic anhydride (tosyl anyhydride), p-nitrobenzenesulfonyl chloride (nosyl chloride) and 4-bromobenzenesulfonyl chloride (brosyl chloride). More particular sulfonating agents that may be mentioned include methanesulfonic anhydride (mesyl anyhydride), methanesulfonyl chloride (mesyl chloride), p-toluenesulfonyl chloride (tosyl chloride) and p-toluenesulfonic anhydride (tosyl anyhydride). In particular embodiments, the sulfonating agent is methanesulfonyl chloride (mesyl chloride).

Other Process Steps

In certain embodiments, the process of the invention comprises additional process steps that may be performed between, during or after steps (i) to (iii) as appropriate.

In particular embodiments, the process further comprises the step of:

(ib) removal (e.g. by filtration) of the or a salt formed between $B^1$ and the leaving group of the sulfonating agent from the solution of a compound of formula II in $S^1$ obtained from step (i).

The skilled person will understand that step (ib) is performed once the reaction of step (i) is complete and before the beginning of step (ii).

Without wishing to be bound by theory, it is believed that step (ib) confers the benefit of preventing the anion formed from the leaving group of the sulfonating agent (e.g. chloride) from taking part in competing nucleophilic substitution processes during step (ii) (to, for example, form the corresponding benzyl chloride of a compound of formula II) which could lead to racemisation of the compound of formula I (through repeated inversions of stereochemistry).

In more particular embodiments, the process further comprises the step of:

(ic) reducing the volume of the solution of the compound of formula II in $S^1$ prior to step (ii).

The skilled person will understand that references to reducing the volume of a solution refer to concentrating the solution through removal of a portion of the solvent. This may be achieved through standard laboratory techniques such as distillation, or, in particular, rotary evaporation.

Reducing the volume of the solution in this manner has the advantage of ensuring that the compound of formula IV remains in solution during step (ii). If too high a proportion of $S^1$ is present in the reaction mixture for step (ii), the compound of formula IV may begin to precipitate, and thereby become unable to participate in the reaction.

The degree to which it is necessary to reduce the volume of the solution of the compound of formula II in $S^1$ may be readily determined by the skilled person and will depend on the concentration at which step (i) was performed. For example, the volume of the solution may be reduced by about 30%, such as about 50% for example about 60-70% (i.e. the volume of the solution may be reduced to around one third of its original volume).

Following the completion of step (ii), the crude product is obtained using standard laboratory practices, such as removal of the solvents (e.g. a mixture of $S^1$ and $S^2$) through rotary evaporation (or distillation as necessary), aqueous work-up and/or precipitation/filtration of byproducts such as unreacted mercaptopyrimidine species. When high-boiling solvents such as N,N-dimethylformamide are present, removing the reaction solvents may involve multiple manipulations such as: concentrating the reaction mixture by rotary evaporation, aqueous work up and, if necessary, distillation at reduced pressure.

In particular embodiments, the process comprises one or more of the steps of:

(iib) concentrating the reaction mixture by rotary evaporation;

(iic) dissolving the residue obtained after step (iib) in a suitable solvent ($S^3$) to cause precipitation of any unreacted mercaptopyrimidine species (compounds of formula IV/V) and filtering the suspension to remove the precipitate;

(iid) dissolving the precipitate obtained from step (iic) in a mixture of water or an aqueous solution (for example a basic solution (e.g. saturated $Na_2CO_3$) and $S^3$, subsequently separating the aqueous and organic layers and combining the organic layer with the filtrate from step (iiic);

(iie) concentrating the combined organic layers by rotary evaporation; and (iif) if necessary, removing residual solvent through distillation under reduced pressure in order to obtain the crude product.

In certain embodiments, $S^3$ is ethyl acetate.

In particular embodiments, the process of the invention further comprises the step of:

(iiib) treating the reaction mixture for step (iii) with a suitable reducing agent in order to reduce any disulfide (VI) formed in the reaction mixture.

(VI)

Suitable reducing agents for use in step (iiib) include $NaBH_4$, $NaB(OAc)_3H$, $NaB(CN)H_3$ and $LiAlH_4$. In preferred embodiments, the reducing agent is $NaBH_4$.

Including step (iiib) in the process of the invention converts the disulfide back to the thiol/thiolate, which is then able to react in step (ii).

In particular embodiments, step (iiib) is performed around room temperature. In such embodiments, the reaction mixture from step (iii) is allowed to cool to room temperature before the reducing agent is added to the reaction.

In particular embodiments, the process of the invention comprises the further step of (iv) treating the crude material obtained from step (ii) (e.g. after one or more of steps (iib) to (iif) have been performed) with a suitable solvent $S^4$ to cause precipitation of the compound of formula I.

As the skilled person will appreciate, step (iv) may also be described as purifying the crude product through trituration with a suitable solvent ($S^4$).

The skilled person will understand that references to the crude material refer to the material obtained after standard organic chemistry manipulations have been performed on the reaction mixture (such as those described in steps (iib) to (iif)) in order to, for example, remove solvents and/or water soluble byproducts, in order to obtain material that is suitable for further purification. In particular, the crude material may be understood to be the material obtained after removal of the reaction solvents and any byproducts that are amenable to removal through precipitation/filtration and/or aqueous work up.

In particular embodiments, $S^4$ is acetonitrile.

Including step (iv) in the process of the invention may further increase the enantiomeric purity of the product as the precipitate appears to be enriched with the major enantiomer compared to the crude product.

In a particular embodiment that may be mentioned, the process comprises the following combination of steps, which steps are as defined herein:
I. steps (i) (sulfonation) and (iii) (generation of the thiolate anion), which are performed concurrently; then
II. step (ib) (filtration to remove the insoluble salt formed during step (i)) and, optionally, step (ic) (reduction of the volume of solution of the compound of formula II in $S^1$); and
III. optionally step (iiib) (reduction of the disulfide);
IV. step (ii) (nucleophilic substitution to produce a compound of formula I), comprising the dropwise addition of the solution obtained after step (ib) (or, if included, step (ic)) to the solution obtained after step (iii) (or, if included, step iiib)
V. step (iv) (precipitation of the compound of formula I).

Specific Enantiomers

As described above, the process of the invention generates single enantiomers of the compound of formula I, depending on the enantiomeric purity of the starting material (the compound of formula II and, ultimately the compound of formula III from which it derives).

Accordingly, the process is for the production of a compound of formula Ia or Ib, or a salt thereof,

(Ia)

(Ib)

wherein $R^1$ and $R^2$ are as defined hereinabove.

As inversion of stereochemistry occurs during step (ii), the skilled person will understand that a compound of formula Ia is produced through the reaction of a compound of formula IIa, and that a compound of formula Ib is produced through the reaction of a compound of formula IIb, wherein $R^1$ and $R^2$ are as defined hereinabove.

Compounds IIa and IIb are produced in step (i) of the process from the corresponding compounds of formula IIIa and IIIb wherein $R^1$ and $R^2$ are as defined hereinabove.

In a particular embodiment, the process is for the production of a compound of formula Ia.

In particular embodiments, the compound of formula I (i.e. the compound of formula Ia or Ib (e.g. Ia)) has a chiral purity of greater than 96%, preferably greater than 99%, more preferably greater than 99.5%, for example 99.7%.

In more particular embodiments that may be mentioned, the process is for the production of 6-amino-2-{[(1S)-1-phenylethyl]sulfanyl}pyrimidin-4-ol, or a salt thereof.

According to the process of the invention, 6-Amino-2-{[(1S)-1-phenylethyl]sulfanyl}pyrimidin-4-ol, or a salt thereof, may be produced with a chiral purity of greater than 96%, preferably greater than 99%, more preferably greater than 99.5%, for example 99.7%.

Further Processes

Compounds produced according to the process of the invention (i.e. compounds of formula I, Ia or Ib (in particular Ia)) may be useful as synthetic intermediates in the production of pharmaceutically-active molecules.

Accordingly, in a second as aspect of the invention, there is provided a process for the preparation of a compound of formula VII, or a salt thereof,

(VII)

wherein $R^1$ and $R^2$ are as defined hereinabove, wherein the process comprises the process of the invention as defined hereinabove (i.e. a process comprising steps (i) to (iii) (optionally including one or more of the additional process steps described herein), and optionally step (iv) as defined hereinabove).

In particular embodiments of the second aspect of the invention, the process further comprises the steps of

(v) The preparation of a compound of formula VIII, or a salt thereof, (VIII)

wherein $R^1$ and $R^2$ are as defined hereinabove, by reacting a compound of formula I, as defined hereinabove, with a suitable thiocyanate salt (for example LiSCN, NaSCN, or, particularly, KSCN) in the presence of bromine, a suitable base (e.g. 2,6-lutidine, or, particularly, pyridine) and a suitable solvent (for example a polar aprotic solvent, such as those mentioned hereinabove, particularly N,N-dimethylformamide).

(vi) The preparation of a compound of formula IX, or a salt thereof, (IX)

wherein $R^1$ and $R^2$ are as defined hereinabove, by reacting a compound of formula VIII in the presence of a suitable base (for example, LiOH, KOH, CsOH, or particularly NaOH) and a suitable solvent (for example a polar aprotic solvent, such as those mentioned hereinabove, particularly N,N-dimethylformamide) at a temperature of about 80° C. to about 150° C. (such as about 100° C. to about 140° C., for example about 110° C. to about 130° C. (e.g. about 120° C.)).

(vii) The preparation of a compound of formula X, or a salt thereof, (X)

wherein $R^1$ and $R^2$ are as defined hereinabove, by reacting a compound of formula IX in the presence of a suitable chlorinating agent (e.g. $SOCl_2$, or, particularly, $POCl_3$), N,N-dimethylformamide and a suitable solvent (for example tetrahydrofuran, 2-methyltetrahydrofuran or, particularly 1,4-dioxane), at a temperature of about 40° C. to about 80° C. (such as about 50° C. to about 75° C., for example about 60° C. to about 70° C. (e.g. about 65° C.))

(viii) The preparation of a compound of VII, as defined hereinabove, by reacting a compound of formula X with leucinol (leucinol)

in the presence of a suitable base (e.g. triethylamine or, particularly, N,N-diisopropylethylamine) and a suitable solvent (for example a polar aprotic solvent, such as those mentioned hereinabove, particularly N-methyl-2-pyrrolidone) at a temperature of about 80° C. to about 150° C. (such as about 100° C. to about 140° C., for example about 110° C. to about 130° C. (e.g. about 120° C.)).

In further embodiments that may be mentioned, the process further comprises the formation of a HCl salt (e.g. the mono HCl salt) of the compound of formula VII, by treating a compound of formula VII with HCl in the presence of a suitable solvent (for example methyl ethyl ketone.

In particular embodiments, the compound of formula VII is a single stereoisomer.

References herein to compounds being produced as single stereoisomers may be understood to indicate that the compound is produced as single diastereomer (e.g. in the case of compound VII the (R,S)-diastereomer) and a single enantiomer of that diastereomer.

Unless otherwise specified, references to single stereoisomers herein (and similarly to stereoisomers being present in pure form, and the like) may be understood to indicate a chiral purity of at least about 90%, such as at least about 95%, for example at least about 97%. More particularly, a single stereoisomer may have a chiral purity of at least about 99.5%, such as at least about 99.7%.

As used herein, chiral purity may be understood to indicate the amount (% w/w) of a single stereoisomer (i.e. diastereomer and/or enantiomer) in the relevant batch of compound.

In particular embodiments, the compound of formula VII is 2-[(2-amino-5-[(1-phenylethyl)thio][1,3]thiazolo[4,5-d]pyrimidin-7-yl)amino]-4-methylpentan-1-ol, or a salt thereof In more particular embodiments, the compound of formula VII is (2R)-2-[(2-amino-5-{[(1S)-1-phenylethyl]thio}[1,3]thiazolo[4,5-d]pyrimidin-7-yl)amino]-4-methylpentan-1-ol, or a salt thereof.

The skilled person will understand that the stereochemistry of the chiral centre marked '1' can be controlled by selecting either enantiomer of leucinol (d-leucinol is used to provide the desired (R)-stereochemistry at this centre). As described above, the stereochemistry at the chiral centre marked 2 is dependent on the stereochemistry of the chiral benzyl alcohol used as the starting material for step (i) (the compound of formula III). The process of the invention provides a scalable route for achieving higher chiral purity at this stereocentre.

In particular embodiments of the second aspect of the invention, the (2R)-2-[(2-amino-5-{[(1S)-1-phenylethyl]thio}[1,3]thiazolo[4,5-d]pyrimidin-7-yl)amino]-4-methylpentan-1-ol has a chiral purity of greater than 99.2%, preferably greater than 99.5%. (e.g. 99.7%).

Compounds with Improved Chiral Purity

The methods disclosed herein provide scalable route to compounds of higher chiral purity than those obtainable using previously disclosed methods.

Accordingly, in a third aspect of the invention, there is provided the compound 6-amino-2-{[(1S)-1-phenylethyl]sulfanyl}pyrimidin-4-ol, or a salt thereof, wherein the compound has a chiral purity of greater than 99.1%, preferably greater than 99.5%.

In a fourth aspect of the invention, there is provided the compound (2R)-2-[(2-amino-5-{[(1S)-1-phenylethyl]thio}[1,3]thiazolo[4,5-d]pyrimidin-7-yl)amino]-4-methylpentan-1-ol, or a salt thereof, wherein the compound has a chiral purity of greater than 99.8%.

Pharmaceutical Formulations

Compounds of formula VII, in particular (2R)-2-[(2-amino-5-{[(1S)-1-phenylethyl]thio}[1,3]thiazolo[4,5-d]pyrimidin-7-yl)amino]-4-methylpentan-1-ol, or a salt thereof, may be useful as pharmaceuticals. As such, these compounds may be formulated into a pharmaceutically acceptable formulation using standard procedures.

In a fifth aspect of the invention there is provided a process for preparing a pharmaceutical formulation comprising (2R)-2-[(2-amino-5-{[(1S)-1-phenylethyl]thio}[1,3]thiazolo[4,5-d]pyrimidin-7-yl)amino]-4-methylpentan-1-ol, or a salt thereof, (or another suitable compound of formula VII, or salt thereof) which process is characterised in that it includes as a process step (in particular steps (i) to (iv), including additional steps such as step (ib) and (iiib) and others). The skilled person will know that such pharmaceutical formulations will comprise/consist of a mixture of active ingredient and, optionally, one or more pharmaceutically acceptable excipient, adjuvant, diluent and/or carrier).

In a sixth aspect of the invention, there is provided a process for the preparation of a pharmaceutical formulation comprising (2R)-2-[(2-amino-5-{[(1S)-1-phenylethyl]thio}

[1,3]thiazolo[4,5-d]pyrimidin-7-yl)amino]-4-methylpentan-1-ol, or a salt thereof, (or another suitable compound of formula VII, or a salt thereof), which process comprises bringing into association (2R)-2-[(2-amino-5-{[(1S)-1-phenylethyl]thio}[1,3]thiazolo[4,5-d]pyrimidin-7-yl)amino]-4-methylpentan-1-ol, or a salt thereof, (or another suitable compound of formula VII, or salt thereof) (which may be formed by a process as hereinbefore described), with (a) one or more pharmaceutically acceptable excipient (e.g. adjuvant, diluent and/or carrier).

The processes described herein have the advantage of being more efficient and more suitable for use in large scale synthesis than the processes of the prior art. In particular, the processes have the advantage of providing a scalable method of the production of pharmaceutically-active compounds with excellent chiral purity.

The compounds produced have the advantage of having higher chiral purity than those accessible by other scalable synthetic routes.

EXAMPLES

Abbreviations

DIPEA N,N-diisopropylethylamine
DMF N,N-dimethylformamide
HPLC high pressure liquid chromatography
MEK methyl ethyl ketone
MTBE methyl tert-butyl ether
NMP N-methyl-2-pyrrolidone
NMR nuclear magnetic resonance
MS mass spectrometry Example 1—Preparation of 6-amino-2-{[(1S)-1-phenylethyl]sulfanyl}pyrimidin-4-ol (1)

Generation of Thiolate Anion:
A 250 mL roundbottomed flask was charged with NaOH flakes (600 mg, 15.00 mmol), 6-amino-2-thioxo-1H-pyrimidin-4-one (Ark Pharm, 95+%, 2.37 g, 15.75 mmol) and DMF (30 mL). The flask was fitted with a condenser. The mixture was stirred at 65° C. (start 13:25). After 1 h 30 min the mixture was allowed to cool down to RT and NaBH$_4$ (174 mg, 4.50 mmol, 30%) was added (15:10) in order to reduce any disulfide formed. The mixture was stirred at RT for 1 h 50 min.

Generation of Mesylate:
In parallel with the reaction described above (R)-1-phenylethyl mesylate in MTBE was prepared as follows:
To a stirred solution of (R)-1-phenylethanol (Ark Pharm, 98%, 1.87 g, 15.00 mmol) and triethylamine (Aldrich, 99.5%, 1.60 g, 15.75 mmol) in MTBE (15 mL) was added dropwise, over 14 min, at ice-bath temperature, a solution of mesyl chloride (Lancaster, 98%, 1.84 g, 15.75 mmol) in MTBE (10 mL). The mixture was stirred at ice-bath temperature for 20 min. The formed Et$_3$NHCl salt was filtered off and the filter cake was washed with ca. 10 mL MTBE. The MTBE solution was concentrated to ca. 10 mL.

Figure 1:
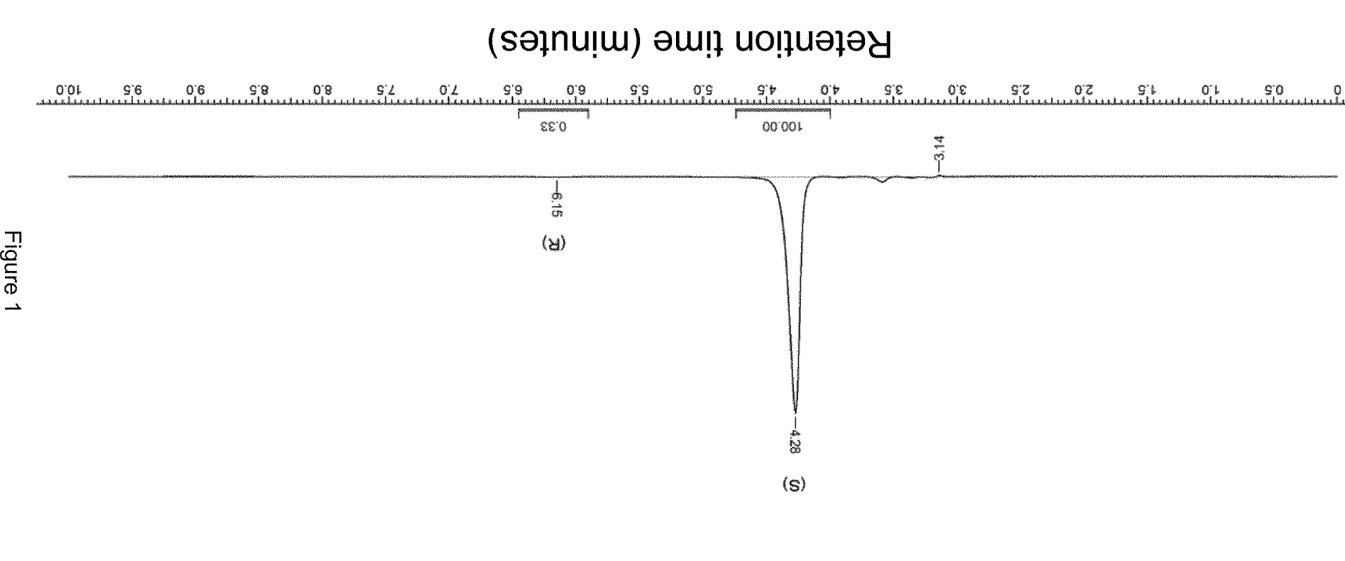
FIG. 1 shows the chiral HPLC trace for the product obtained following the process described in Example 1.

Alkylation Step:
The MTBE solution containing the mesylate was added dropwise to the DMF solution containing the 6-amino-2-thioxo-1H-pyrimidin-4-one anion over 10 min at ice-bath temperature (17:10). The mixture was allowed to slowly warm up to RT and was stirred at RT overnight. Work up after 17.5 h: The mixture was concentrated to a small volume. EtOAc (ca. 50 mL) was added, which resulted in heavy precipitation of 6-amino-2-thioxo-1H-pyrimidin-4-one. The mixture was sonicated by ultrasound and then the solid was filtered off and the filter cake was washed with EtOAc (ca. 10 mL). The solid was suspended in sat. NaHCO$_3$ (15 mL) and EtOAc (20 mL) was added. The resulting suspension was sonicated and filtered down into a separatory funnel. The phases were separated and the aqueous phase was discarded. The organic phase containing product was combined with the EtOAc filtrate. The combined organic phases were washed with sat. NaHCO$_3$ (10 mL), dried over MgSO$_4$, filtered and evaporated. The last residue of DMF was distilled off (78° C./18 mbar) to yield 4.38 g of crude product as a light yellow viscous oil. CH$_3$CN (11 mL) was added to the oil and the resulting solution was ultrasound sonicated and heavy precipitation was observed after a few minutes. The mixture was digested at 75° C. for 45 min. The mixture was allowed to slowly cool down to RT and the solid was collected by filtration and was washed with ice-cold CH$_3$CN (ca. 5 mL). The resulting white solid material was dried in a vacuum oven at 40° C. for 2.5 days. Yield: 1.861 g. $^1$H NMR (600 MHz, CD$_3$OD) δ ppm 7.43-7.47 (m, 2H) 7.31-7.35 (m, 2H) 7.23-7.28 (m, 1H), 5.12 (q, J=7.1 Hz, 1H) 5.06 (s, 1H) 1.75 (d, J=7.0 Hz, 3H). MS (ESI+) m/z 248 [M+H]$^+$.
HPLC purity: ca. 94%
HPLC chiral purity: 99.7% (S), i.e. 99.4% e.e. The chiral HPLC trace is reproduced in FIG. 1.
Measured on an Astec CHIROBIOTIC T column (250× 4.6 mm, 5 μm), Eluent: 100% MeOH, Agilent 1100 system.
$^1$H NMR: appears pure, except for some residual solvent (MeCN: 0.03% (w/w), DMF: 0.16% (w/w))

Example 2—Preparation of 6-amino-2-{[(1S)-1-phenylethyl]sulfanyl}pyrimidin-4-ol (1) (50 mmol Scale)

Generation of Thiolate Anion:

A 250 mL round-bottomed flask was charged with NaOH flakes (2.00 g, 50.00 mmol), 6-amino-2-thioxo-1H-pyrimidin-4-one (Ark Pharm, 95+%, 7.91 g, 52.50 mmol) and DMF (100 mL). The flask was fitted with a condenser. The mixture was stirred at 65° C. (start 11:00). After 2 h 30 min the mixture was allowed to cool down to RT and NaBH$_4$ (567 mg, 15.00 mmol, 30%) was added (14:10) in order to reduce any disulfide formed. The mixture was stirred at RT for 40 min.

Generation of Mesylate:

In parallel with the reaction described above (R)-1-phenylethyl mesylate in MTBE was prepared as follows:

To a stirred solution of (R)-1-phenylethanol (Ark Pharm, 98%, 6.23 g, 50.00 mmol) and triethylamine (Aldrich, 99.5%, 5.34 g, 52.50 mmol) in MTBE (50 mL) was added dropwise, over 10 min, at ice-bath temperature, a solution of mesyl chloride (Lancaster, 98%, 6.14 g, 52.50 mmol) in MTBE (30 mL). The mixture was stirred at ice-bath temperature for 20 min. The formed Et$_3$NHCl salt was filtered off and the filter cake was washed with ca. 20 mL MTBE. The MTBE solution was concentrated to ca. 25 mL.

Alkylation Step:

The MTBE solution containing the mesylate was added dropwise to the DMF solution containing the 6-amino-2-thioxo-1H-pyrimidin-4-one anion over 20 min at ice-bath temperature (15:05). The mixture was allowed to slowly warm up to RT and was stirred at RT overnight. Work up after 19 h: The mixture was concentrated to a small volume, so that almost all of the DMF was removed. EtOAc (120 mL) was added, which resulted in heavy precipitation of 6-amino-2-thioxo-1H-pyrimidin-4-one. The mixture was sonicated by ultrasound and then the solid was filtered off and the filter cake was washed with EtOAc (ca. 30 mL). The solid was suspended in sat. Na$_2$CO$_3$ (50 mL) and EtOAc (70 mL) was added. The resulting suspension was stirred until all of the material was dissolved, and it was then transferred to a separatory funnel. The phases were separated and the aqueous phase was discarded. The organic phase containing product was combined with the EtOAc filtrate. The combined organic phases were washed with sat. NaHCO$_3$ (25 mL), water (15 mL), brine (15 mL), dried over MgSO$_4$, filtered and evaporated. The last residue of DMF was distilled off (78° C./18 mbar) to yield 13.32 g of crude product as a light yellow semi solid. CH$_3$CN (35 mL) was added to the to the crude material and the resulting suspension was ultrasound sonicated. The mixture was digested at 75° C. for 30 min. The mixture was allowed to slowly cool down to RT and the solid was collected by filtration and was washed with ice-cold CH$_3$CN (ca. 10 mL). The resulting white solid material was dried in a vacuum oven at 40° C. for 2 days. Yield: 6.168 g (50%) of product as a white solid. $^1$H NMR (600 MHz, CD$_3$OD) δ ppm 7.43-7.47 (m, 2H) 7.31-7.35 (m, 2H) 7.23-7.28 (m, 1H), 5.13 (q, J=7.0 Hz, 1H) 5.06 (s, 1H) 1.75 (d, J=7.0 Hz, 3H). MS (ESI+) m/z 248 [M+H]$^+$.

HPLC purity: 96.5%

Figure 2:
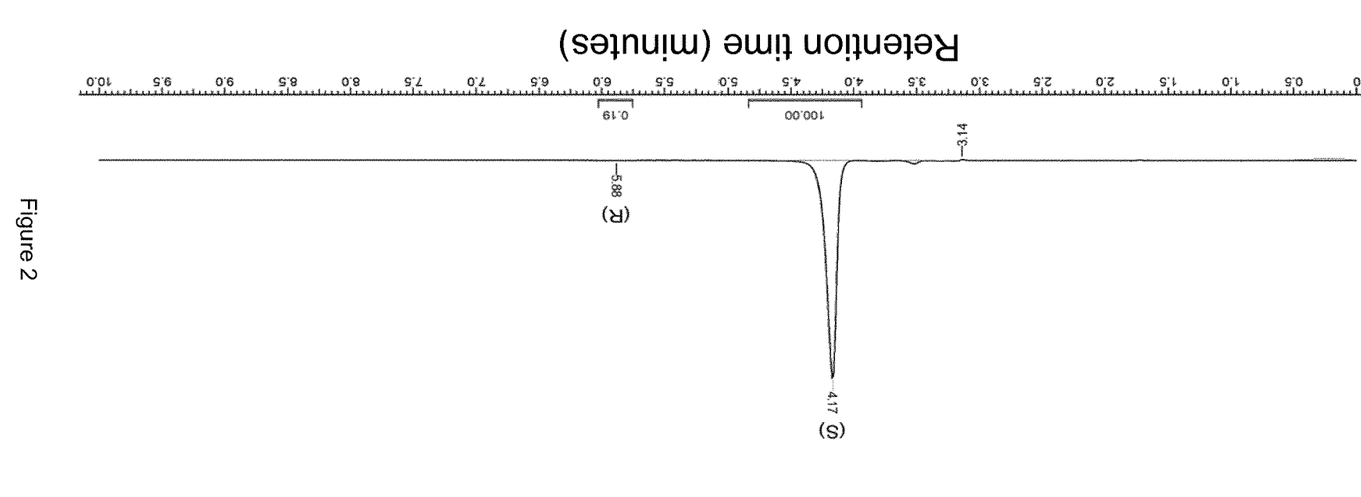
FIG. 2 shows the chiral HPLC trace for the product obtained following the process described in Example 2.

HPLC chiral purity: 99.8% (S), i.e. 99.6% e.e. (The peak corresponding to the R-isomer can hardly be detected. The integral is uncertain, due to the baseline noise). The chiral HPLC trace is reproduced in FIG. 2.

Measured on an Astec CHIROBIOTIC T column (250× 4.6 mm, 5 µm), Eluent: 100% MeOH, Agilent 1100 system.

$^1$H NMR: Appears pure except for some residual solvent (MeCN: 0.41% (w/w) DMF: 0.23% (w/w)).

Example 3—Preparation of (2R)-2-[(2-amino-5-{[(1S)-1-phenylethyl]thio}[1,3]thiazolo[4,5-d]pyrimidin-7-yl)amino]-4-methylpentan-1-ol·HCl

3.1 Preparation of 4-amino-6-hydroxy-2-{[(1S)-1-phenylethyl]sulfanyl}pyrimidin-5-yl thiocyanate (2)

Compound 1 (1.63 g, 6.59 mmol) and KSCN (1.92 g, 19.8 mmol) were dissolved in DMF (20 mL) in a 100 mL flask. The mixture was heated to 65° C. until all of the starting material had dissolved. Pyridine (886 mg, 12.35 mmol) in DMF (2 mL) was added. The reaction mixture was cooled to 4° C. and bromine (1.219 g, 7.62 mmol) in DMF (3 mL) was added dropwise (15:12) over 10 min leading to some precipitation. The mixture was stirred at 4-10° C. for 1 h 15 min when HPLC indicated complete conversion to product. The reaction was allowed to warm up to RT and 5 mL of 15% Na$_2$S$_2$O$_5$ (sodium metabisulfite) was added together with water (2 mL). The mixture was stirred at 60° C. for 10 min. Then at RT more water (25 mL) was added. Stir at RT overnight. The solid product was collected by filtration, washed with cold water and dried for 4.5 h in vacuum at 60° C. Yield: 1.806 g (90%) of 98% pure product as a light yellow solid. 1H NMR (600 MHz, CD$_3$OD) δ ppm 7.44-7.48 (m, 2H) 7.32-7.36 (m, 2H) 7.25-7.29 (m, 1H) 5.14 (q, J=7.1 Hz, 1H) 1.77 (d, J=7.3 Hz, 3H). MS (ESI+) m/z 305 [M+H]$^+$.

$^1$H NMR: appears very pure. The only visible contamination is DMF (ca. 0.36% w/w)

3.2 Preparation of 2-amino-5-{[(1S)-1-phenylethyl]sulfanyl}[1,3]thiazolo[4,5-d]pyrimidin-7-ol (3)

Compound 2 (1.80 g, 5.91 mmol was slurried in DMF (16 mL) and 2M NaOH (6 mL, 12 mmol) was added dropwise at RT. The mixture turned red-brown upon addition of NaOH and the slurry was dissolved. Heat to 120° C. (13:20) (HPLC after 3 h: 100% conversion to product).

Work up: The mixture was allowed to cool to RT, and water (20 mL) was added=>slight precipitation. The pH of the reaction mixture was adjusted to ca. pH 4-5 by addition of conc. HCl. The solid was collected by filtration and washed with two portions of water (2×8 mL) and dried in vacuum at 60° C. to yield 1.687 g (94%) of product as an off-white solid. 1H NMR (600 MHz, CD3OD) δ ppm 7.45-7.49 (m, 2H) 7.31-7.35 (m, 2H) 7.24-7.28 (m, 1H) 5.21 (q, J=7.1 Hz, 1H) 1.79 (d, J=7.0 Hz, 3H). MS (ESI+) m/z 305 [M+H]+.

HPLC: ca. 94% purity

¹H NMR: Looks pure but some DMF present. Integrals indicate 0.55% (w/w).

3.3 Preparation of 7-chloro-5-{[(1S)-1-phenylethyl]sulfanyl}[1,3]thiazolo[4,5-d]pyrimidin-2-amine (4)

To a slurry of compound 3 (1.82 g, 5.98 mmol) in dioxane (15 mL) were added DMF (962 mg, 13.2 mmol) in dioxane (2.5 mL) and POCl₃ (3.03 g, 19.7 mmol) in dioxane (2.5 mL) at RT (start: 14:00). After 30 min the slurry had dissolved into a light brown homogeneous solution. HPLC after 0.5 h at RT shows the imine formed by DMF and the starting material (68%), and imine formed by the product and DMF (32%). The reaction mixture was then heated at 65° C. (start: 13:40). HPLC after 3 h at 65° C. shows complete conversion to imine formed by DMF and the product. The reaction mixture was allowed to cool to RT and water (5 mL) was added. The temperature was raised to 65° C. (17:40). After stirring for 10 min at this temperature all of the product-imine was hydrolyzed. The mixture was cooled to RT. Water (10 mL) was added and the mixture was evaporated to about half the volume. The pH was adjusted to ca. 6-7 with sat. NaHCO₃ and solid NaHCO₃. The resulting phase was extracted with EtOAc (3×25 mL) and the combined organic phases were washed with sat. Na₂CO₃ (2×6 mL), water (6 mL) and brine (6 mL), dried over Na₂SO₄ and evaporated to yield 1.746 g (98%) of >97% pure product as an light orange solid. ¹H NMR (600 MHz, CD₃OD) δ ppm 7.44-7.49 (m, 2H) 7.28-7.33 (m, 2H) 7.20-7.25 (m, 1H) 5.06 (q, J=7.1 Hz, 1H) 1.75 (d, J=7.3 Hz, 3H). MS (ESI+) m/z 323 [M+H]+.

¹H NMR: Looks very pure, but still solvent present. DMF: 2.7% (w/w), EtOAc: 1.8% (w/w), dioxane: 1.8% (w/w).

Yield corrected for solvent content: ca. 5.065 g (92%).

3.4 Preparation of (2R)-2-[(2-amino-5-{[(1S)-1-phenylethyl]thio}[1,3]thiazolo[4,5-d]pyrimidin-7-yl)amino]-4-methylpentan-1-ol·xHCl (5)

Compound 4 (1.852 g, 5.74 mmol), DIPEA (1.112 g, 8.61 mmol) and D-leucinol (1.008 g, 8.61 mmmol) were dissolved in NMP (12 mL) and the mixture was stirred at 120° C. in a sealed pyrex tube (start: 17:40).

HPLC after 15.5 h: ca. 98% conversion

HPLC after 19.5 h: >99% conversion

Work up: Ice water was poured into the mixture. Initially a solid was formed, but at the end of the addition the solid collapsed to a dark brown oil. EtOAc (50 mL) was added and the phases were separated. The aqueous phase was extracted with EtOAc (2×25 mL), and the combined organic phases were washed with water (8 mL), sat. NaHCO₃ (3×8 mL), water (8 mL) and brine (8 mL), dried over MgSO4, filtered and evaporated. Dried in vacuum to yield 2.697 g of crude material as a brown oil. HPLC purity: ca. 92%. The oil was dissolved in MEK (ca. 18 mL) and conc. HCl (12.5 M, 574 µL, 7.18 mmol) was added. There was no spontaneous precipitation of the HCl salt. The mixture was gently stirred at RT and after ca. 20 min precipitation occurred. The mixture was stirred gently for 2.5 h and the solid was isolated by filtration on a P3 sintered glass filter. The solid was washed with three portions of MEK and was then dried in vacuum at 60° C. for 2.5 days. Yield (batch 1): 1.224 g (48.5%) of the product as hydrochloride salt.

HPLC purity: 99.0% (basic method); 97.4% (acidic method).

A substantial amount of solids passed through the filter into the filtrate. The solids were isolated by centrifugation and the supernatant was removed by pipette. The solid was washed with two portions (ca. 2×5 mL) of MEK. After the last supernatant was removed the product was dried in vacuum at 60° C. for 2.5 days. Yield (batch 2): 324 mg (12.8%) of the product as hydrochloride salt.

HPLC purity: 99.0% (basic method); 97.5% (acidic method).

Combined yield: 1.548 g (61.3%)

Both batches contain ca. 0.07% DMF (w/w). The DMF was already present in the starting material.

Further Purification of the Combined Batches

The two batches of compound 5 were combined (1.338 g, 3.041 mmol) in a 50 mL roundbottomed flask and water (6 mL) was added followed by 2M NaOH (1.6 mL, 3.2 mmol). The mixture was stirred and EtOAc (40 mL) was added. An additional 0.5 mL (1 mmol) 2M NaOH was added during stirring. After 15 min all of the solids were dissolved and the phases were separated. The pH of the aqueous phase was measured with a pH stick=>pH=7. More 2M NaOH (0.4 mL, 0.8 mmol) was added to the aqueous phase resulting in a pH of 10. The aq. phase was extracted with EtOAc (25 mL) and the phases were separated. The combined organic phases were dried over Na$_2$SO$_4$, filtered and evaporated to yield the free base as a crystalline beige solid. The free base was dissolved in MEK (15 mL) and HCl (37%, 12.5 M, 255 µL, 3.19 mmol) was added during stirring. A white precipitate was immediately formed. The mixture was stirred gently for 2 h and the solid was collected by filtration on a P4 sintered glass filter. The solids were washed with MEK (5 mL) and dried in vacuum at 60° C. for 3 h. Yield: 1.187 g (89% based on the unpurified material) of 99% pure product as a white solid. $^1$H NMR (600 MHz, CD30D) 6 ppm 7.49 (d, J=7.3 Hz, 2H) 7.37 (t, J=7.6 Hz, 2H) 7.27-7.32 (m, 1H) 5.23 (q, J=7.0 Hz, 1H) 4.60-4.70 (m, 1H) 3.55 (d, J=5.5 Hz, 2H) 1.83 (d, J=7.3 Hz, 3H) 1.67-1.76 (m, 1H) 1.58-1.65 (m, 1H) 1.48-1.54 (m, 1H) 1.00 (d, J=6.7 Hz, 3H) 0.98 (d, J=6.7 Hz, 3H). MS (ESI+) m/z 404 [M+H]$^+$ The diasteromeric ratio of the final product reflects the enantiomeric ratio of the starting material (compound 1), which was 99.7% (S).

$^1$H NMR: The spectrum looks very pure. Trace amounts of DMF were, however, detected.

Comparative Example 4—Process scale two-step procedure for the synthesis of 6-amino-2-{[(1S)-1-phenylethyl]sulfanyl}pyrimidin-4-ol (1)

Step 1

A dry 1380 L glass lined reactor was charged at Ti=20° C. with ethyl acetate and (s)-phenyl ethanol under nitrogen atmosphere. The clear to yellow solution was kept at Ti=20° C. for 30 minutes then discharged to 200 L poly lined drums. To the 1380 L glass lined reactor was charged cyanuric chloride, ethyl acetate (1.2) and N,N-dimethylformamide within 60 minutes. The solution was heated from Ti=6.3° C. to Ti=25° C. within 25 minutes then cooled to Ti=−5° C. within 180 minutes. By use of a 1″ diaphragm pump, the premade solution of (s)-phenylethanol in ethyl acetate was charged within 12 hours at a maximum Ti=−0.4° C. then kept at Ti=−5° C. for 3 hours. IPC sample indicated (s)-phenyl ethanol=0.35% (Target<1%). Propan-2-ol was charged within 120 minutes at Ti=−5° C. and kept for 30 minutes, celite was charged and then filtered on a stainless steel nutsche filter equipped with 50 µm cloth, significant filtration problems encountered due to the cloth blinding, material was recharged portion wise to a 50 L pressure filter with 50 µm cloth with celite bed. The solid was washed with ethyl acetate on portionwise filtration. Filtration liquors were recharged to the 1380 L vessel and set for distillation at maximum Ti=40.9° C. and vac 200 mbar removing 750 kg distillate. The vessel was cooled to Ti<25° C. and filtered portionwise on a 50 L pressure filter equipped with 50 µm cloth and celite bed, portionwise washing with ethyl acetate. Filtration liquors were recharged to a 330 L vessel and set for distillation at maximum Ti=35.1° C. and vac 24 mbar removing 500 kg distillate. 275 kg was isolated as a pale-yellow liquid.

Result:

275 kg uncorrected:

GC Purity: 73.87% (area %)

GC Chiral Purity: 94.9% (area %, R Isomer).

Step 2

A dry 2800 L glass lined reactor was charged at Ti=20° C. with N,N-dimethylformamide, sodium hydroxide pellets and 4-Amino-6-hydroxy-2-mercapropyrimidine within 60 minutes maintaining the temperature below Ti=25° C. Heated to Ti=62.5° C. within 60 minutes and kept for 30 minutes. (1R)-phenylethyl chloride was charged within 75 minutes maintaining Ti=60-65° C. The reaction was kept at Ti=60-70° C. for 6 hours. IPC sample indicated 4-Amino-6-hydroxy-2-mercapropyrimidine=<0.1% (Target<1%). Reaction cooled to Ti<25° C. and charged water, pH adjusted to 12.01 using 32% Sodium hydroxide within 90 minutes. Charged Toluene and kept for 30 minutes followed by filtration to remove interphase solids using a stainless steel nutsche filter equipped with 50 µm cloth and celite bed within 3 hours. After recharging the filtrate phase separated to remove the lower aqueous phase (1500 L) organic phase was retained as waste. The aqueous phase was charged to a 1380 L glass lined reactor and set for distillation at maximum Ti=61.3° C. and vac 180 mbar removing 1800 L distillate. Water charged and then heated to Ti=65.3° C. within 90 minutes. pH adjusted with 6.2% hydrochloric acid to pH 5.5 within 180 minutes. Cooled to Ti<20° C. within 180 minutes then filtered on a stainless steel nutsche filter, equipped with 50 µm cloth, within 10 hours. Pull dried and displacement washed to isolate damp off white solid 588 kg.

Result:

588 kg uncorrected (LOD Content 30% w/w=176.4 Kg, Yield (Corr): 48.1%)

HPLC Purity: 81.26% (area %)

HPLC Chiral Purity: 95.03% (area % S Isomer)

First Recrystallisation

A dry 2800 L glass lined reactor was charged at Ti=20° C. with 4-Amino-6-hydroxy-2-[(1S)-1-(phenylethyl)thio]pyrimidine and methanol, heated to Ti=55° C. within 120 minutes and kept for 1 hours. By method of in-line GAFF filter the solution was transferred at Ti=55° C. to a 4500 L glass lined vessel, on completion washed lines through with methanol. Heat applied to Ti=65° C. (reflux) and kept for 1 hour, charged water within 3 hours maintaining Ti>60° C. Agitation reduced and cooled slowly to Ti=22.5° C. within 6 hours. Filtered on stainless steel nutsche filter equipped with 50 μm cloth within 12 hours, pull dried and displacement washed pull dried to isolate 302 kg of off white solid.

Result:

302 kg uncorrected

HPLC Purity: 95.11% (area %)

HPLC Chiral Purity: 97.09% (area % R Isomer) (area % S Isomer)

Second Recrystallisation

A dry 4500 L glass lined reactor was charged at Ti=20° C. with 4-Amino-6-hydroxy-2-[(1S)-1-(phenylethyl)thio]pyrimidine and methanol, heated to Ti=65° C. (reflux) within 50 minutes and kept for 30 minutes, charged water within 3 hours maintaining Ti>60° C. Agitation reduced and cooled slowly to Ti=23.1° C. within 6 hours. Filtered on stainless steel nutsche filter equipped with 50 μm cloth within 12 hours, pull dried and displacement washed, pull dried to isolate 142 kg of off white solid. Dried in Cone Vac Dryer at maximum Ti=60° C. and 20 mbar.

Result:

106 kg uncorrected (LOD Content 99.1% w/w=105.1 Kg, Yield (Corr): 61.1%)

HPLC Purity: 94.07% (area %)

HPLC Chiral Purity: 99.04% (area % S Isomer)

Summary

Two synthetic steps and two recrystallisations were necessary to achieve a chiral purity of >99%.

The overall yield of the process was 29.3% (including the recrystallisation steps).

The invention claimed is:

1. A compound having a structure:

or a salt thereof, with a chiral purity of greater than 99.7%.

2. The compound as claimed in claim 1, with a chiral purity of at least 99.8%.

3. A pharmaceutical composition comprising a compound having a structure:

or a salt thereof, with a chiral purity of greater than 99.7%.

4. The pharmaceutical composition of claim 3, wherein the compound has a chiral purity at least 99.8%.

* * * * *